United States Patent [19]

Foricher et al.

[11] Patent Number: 6,162,929

[45] Date of Patent: *Dec. 19, 2000

[54] PROCESS FOR THE MANUFACTURE OF BISPHOSPHINE OXIDE AND BISPHOSPHONATE COMPOUNDS

[75] Inventors: Joseph Foricher, Mulhouse, France; Rudolf Schmid, Basel, Switzerland

[73] Assignee: Hoffmann-La Roche Inc., Nutley, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/212,646

[22] Filed: Dec. 15, 1998

[30] Foreign Application Priority Data

Dec. 23, 1997 [EP] European Pat. Off. ............. 97122720

[51] Int. Cl.[7] .............................. C07D 333/50; C07F 9/53
[52] U.S. Cl. .............................. 549/6; 549/216; 549/221; 549/220; 568/14
[58] Field of Search ................... 568/14; 549/6, 549/5, 216, 218, 220, 221; 558/207, 155, 156

[56] References Cited

U.S. PATENT DOCUMENTS

| | | |
|---|---|---|
| 3,032,589 | 5/1962 | Hoffman . |
| 4,683,338 | 7/1987 | Wife . |
| 4,956,055 | 9/1990 | Puckette . |
| 5,274,125 | 12/1993 | Broger ..................................... 549/216 |
| 5,302,738 | 4/1994 | Foricher et al. . |
| 5,430,191 | 7/1995 | Foricher et al. . |
| 5,488,172 | 1/1996 | Cereghetti et al. . |
| 5,510,503 | 4/1996 | Laue .......................................... 556/21 |
| 5,872,273 | 2/1999 | Saito ........................................ 556/21 |

FOREIGN PATENT DOCUMENTS

| | | |
|---|---|---|
| 0 398 132 | 11/1990 | European Pat. Off. . |
| WO 92/16535 | 10/1992 | WIPO . |
| WO 96/01831 | 1/1996 | WIPO . |

OTHER PUBLICATIONS

Helvetica Chimica Acta vol. 74 (1991) pgs. 370–389.
Schmid, R., et al., Helv. Chim. Acta, 74(2):370–389 (1991).
J Chem Soc Chem Commun pp 685–686 by Benincori, Mar. 1995.

*Primary Examiner*—Jean F. Vollano
*Attorney, Agent, or Firm*—George W. Johnston; William H. Epstein; Eileen M. Ebel

[57] ABSTRACT

A process for the manufacture of bisphosphine oxide compounds and bisphosphonates as intermediates for the production of bisphosphine ligands, in which in a single step process a) a phosphine oxide compound is reacted in an organic solvent at −70° C. to 20° C. with 0.5–3 eq. of a lithium or magnesium amide compound, b) 0.5–3 eq. of oxidatively-acting metal salt or metal salt complex are added to the suspension obtained in stage a) in a temperature range of −70° C. to 20° C., with a racemate of a bisphosphine oxide compound being obtained;

c) a racemate cleavage is carried out if desired; and d) the bisphosphonates obtained in stage b) or c) are converted into bisphosphine oxides.

37 Claims, No Drawings

PROCESS FOR THE MANUFACTURE OF BISPHOSPHINE OXIDE AND BISPHOSPHONATE COMPOUNDS

BACKGROUND OF THE INVENTION

Known process for the manufacture of bisphosphine oxide compounds or bisphosphonates of general formulae I and II are two-stage processes. In the first stage a compound of formula Ia or Ia set forth below is converted into the corresponding iodide or bromide with iodine or bromine at about −70° C. in the presence of a lithium dialkylamide. A reagent which yields iodine or bromine, such as e.g. N-iodo- or bromo-succinamide, 1-iodo-2-chloroethane, 1,2-dibromomethane and the like, can also be used in place of iodine or bromine.

Starting materials of formula Ia or IIa in which $R^4$ signifies $C_{1-8}$-alkoxy or phenoxy can also be reacted with an alkyllithium solution, preferably butyllithium solution or sec.butyllithium solution, in the presence of catalytic amounts of an amine, such as e.g. diisopropylamine. If desired, an additional tert.amine, such as e.g. N,N,N',N'-tetramethyldiamine, is added.

Starting materials of formula Ia or IIa in which $R^4$ signifies phenyl, substituted phenyl, naphthyl, substituted naphthyl, heteroaryl or substituted heteroaryl can also be reacted with an aryllithium solution, preferably phenyllithium solution, or an alkyllithium solution, preferably tert-butyllithium solution.

In a second step the aryl halide is converted into a biaryl compound at 110° C. to 200° C. in the presence of copper(0) (Ullmann coupling).

This two-stage process is not very suitable for implementation on an industrial scale. The first stage must be carried out at low temperatures and gives the aryl halide in a yield of about 70%. Precipitates of byproducts which occur can give rise to difficulties. On the other hand, the second stage must be carried out at high temperatures and requires stoichiometric amounts of copper, with the Ullmann coupling also being unfavourable from ecological points of view.

The object of the invention is to provide an improved process for the manufacture of bisphosphine oxide compounds and bisphosphonates.

SUMMARY OF THE INVENTION

The present invention is concerned with a novel process for the manufacture of bisphosphine oxide compounds and bisphosphonates as intermediates for the production of bisphosphine ligands.

In particular, the invention is concerned with a process for the manufacture of compounds of formula I or II

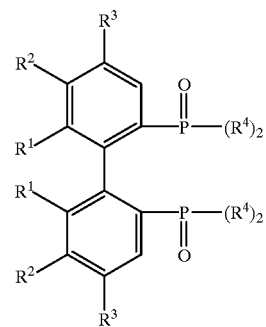

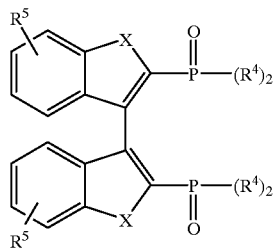

wherein
X signifies O or S;
$R^1$ and $R^2$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; or
$R^1$ and $R^2$ together signify a fused benzene ring, a fused substituted benzene ring, a tetramethylene, trimethylene, methylenedioxy or ethylenedioxy group or a system of formula a

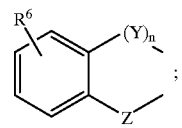

$R^3$, $R^5$, $R^6$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;
$R^4$ signifies $C_{1-8}$-alkoxy, phenyloxy, substituted phenyloxy, $C_{1-8}$-alkyl, $C_{3-7}$-cycloalkyl, phenyl, substituted phenyl, naphthyl, substituted naphthyl, heteroaryl or substituted heteroaryl;
Y signifies $CR^7R^8$, O, S or N-$C_{1-8}$-alkyl;
Z signifies O, S, SO or $SO_2$;
n signifies 0 or 1;
$R^7$, $R^8$ each independently signify hydrogen or $C_{1-8}$-alkyl with the proviso that $R^4$ is not phenyl when $R^1$ and $R^2$ together signify methylenedioxy.

This process for the manufacture of bisphosphine oxide compounds and bisphosphonates as intermediates for the production of bisphosphine ligands is a a single step process in which
a) a phosphine oxide compound is reacted in an organic solvent with a lithium or magnesium amide compound
b) oxidatively-acting metal salt or metal salt complex are added to the mixture obtained in stage a), with a racemate of a bisphosphine oxide compound being obtained;

c) a racemate cleavage is carried out if desired; and
d) the bisphosphonates obtained in stage b) or c) are converted into bisphosphine oxides.

DETAILED DESCRIPTION OF THE INVENTION

The object is achieved by a one-step process using a compound of general formula Ia or IIa

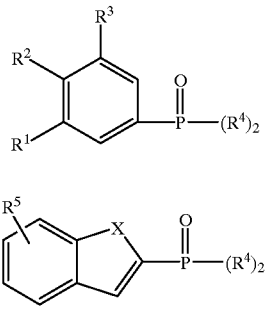

wherein $R^1$, $R^2$, $R^3$, $R^5$ and X have the significances set forth above and $R^4$ signifies $C_{1-8}$-alkoxy, phenyloxy, substituted phenyloxy, phenyl, substituted phenyl, naphthyl, substituted naphthyl, heteroaryl or substituted heteroaryl;

a) in an organic solvent at −70° C. to 20° C., preferably at −30° C. to 0° C., a-1) is reacted with 0.5–3 eq., preferably with 0.9–1.2 eq., of a compound of formula b1 or b2,

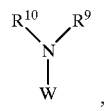

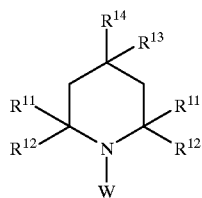

wherein $R^9$ signifies $C_{1-8}$-alkyl, $C_{3-6}$-cycloalkyl or phenyl;

$R^{10}$ signifies $C_{1-8}$-alkyl or $C_{3-6}$-cycloalkyl;

$R^{11}$ and $R^{12}$ signify the same or different $C_{1-8}$-alkyl groups;

$R^{13}$ and $R^{14}$ each independently signify hydrogen or $C_{1-8}$-alkoxy; or $R^{13}$ signifies hydrogen or $C_{1-8}$-alkyl and $R^{14}$ signifies OW; or $R^{13}$ and $R^{14}$ together signify ketal groupings of formulae c–e

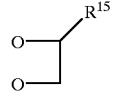
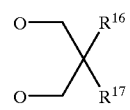

$R^{15}$ signifies $C_{1-8}$-alkyl;

$R^{16}$ and $R^{17}$ signify hydrogen or the same or different $C_{1-8}$-alkyl groups; and W signifies lithium, Mg chloride, bromide, or iodide, or magnesium amide; or a-2) is reacted with catalytic amounts of one of the above-defined compounds of formula b1 or b2 in the presence of a $C_{1-8}$-alkyllithium or aryllithium solution, optionally with the addition of an adjuvant amine; or a-3) a compound of formula Ia or IIa in which $R^4$ signifies phenyl, substituted phenyl, naphthyl, substituted naphthyl, heteroaryl or substituted heteroaryl is reacted with a $C_{1-8}$-alkyllithium or aryllithium solution, preferably with a tert.butyllithium or phenyllithium solution;

b) 0.5–3 eq., preferably 1–1.5 eq., of an oxidatively-acting metal salt or metal salt complex is added to the mixture obtained in stage a) in a temperature range of −70° C. to 20° C., preferably of −30° C. to 20° C., with a racemate of a compound of formula I or II being obtained;

c) a racemate resolution is carried out if desired; and d) the bisphosphonates obtained in stage b) or c) are converted into bisphosphine oxides.

Accordingly, this invention is directed to a process for the manufacture of compounds formula I

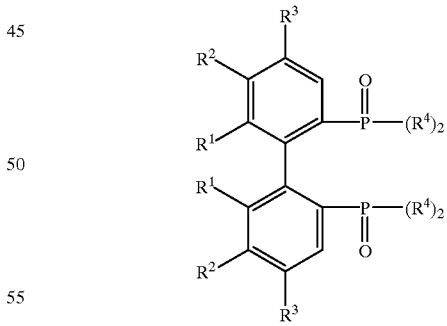

wherein $R^1$ and $R^2$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; or $R^1$ and $R^2$ together signify a fused benzene ring, a fused substituted benzene ring, a tetramethylene, trimethylene, methylenedioxy or ethylenedioxy group or a system of formula a

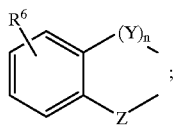

a $R^3$ and $R^6$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;

$R^4$ signifies $C_{1-8}$-alkoxy, phenyloxy, substituted phenyloxy, $C_{1-8}$-alkyl, $C_{3-7}$-cycloalkyl, phenyl, substituted phenyl, naphthyl, substituted naphthyl, heteroaryl, or substituted heteroaryl;

Y signifies $CR^7R^8$, O, S or N-$C_{1-8}$-alkyl;

Z signifies O, S, SO or $SO_2$;

n signifies 0 or 1;

$R^7$, $R^8$ each independently signify hydrogen or $C_{1-8}$-alkyl;

with the proviso that $R^4$ is not phenyl when $R^1$ and R together signify methylenedioxyl in which a compound of formula Ia

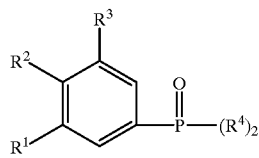

Ia wherein $R^1$, $R^2$, and $R^3$ have the significances set forth above and $R^4$ signifies $C_{1-8}$-alkoxy, phenyloxy, substituted phenyloxy, phenyl, substituted phenyl, naphthyl, substituted naphthyl, heteroaryl, or substituted heteroaryl;

is reacted with a compound of formula b1 or b2 in an organic solvent

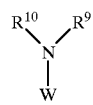

b1

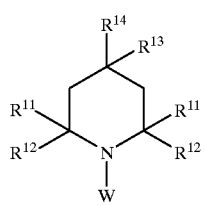

b2 wherein $R^9$ signifies $C_{1-8}$-alkyl, $C_{3-6}$-cycloalkyl or phenyl;

$R^{10}$ signifies $C_{1-8}$-alkyl or $C_{3-6}$-cycloalkyl;

$R^{11}$ and $R^{12}$ signify the same or different $C_{1-8}$-alkyl groups;

$R^{13}$ and $R^{14}$ each independently signify hydrogen or $C_{1-8}$-alkoxy; or $R^{13}$ signifies hydrogen or $C_{1-8}$-alkyl and $R^{14}$ signifies OW; or $R^{13}$ and $R^{14}$ together signify ketal groupings of formulae c–e

c

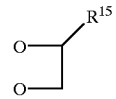

d

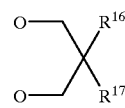

e $R^{15}$ signifies $C_{1-8}$-alkyl;

$R^{16}$ and $R^{17}$ signify hydrogen or the same or different $C_{1-8}$-alkyl groups; and W signifies lithium, magnesium chloride, bromide, or iodide, or magnesium amide; and an oxidatively-acting metal salt or metal salt complex is added to the resulting mixture to provide a compound of formula 1.

In a preferred such process, the amount of the compound of formula b1 or b2 is 0.5 to 3.0 eq., especially 0.9 to 1.2 eq. In another preferred process, a catalytic amount i.e. 1 to 50 mol %, preferably 5 to 20 mol % of the compound of formula b1 or b2, preferably is used in the presence of $C_{1-8}$ alkyllithium or aryllithium (such as tert-butyllithium or phenyllithium. A tert. amine or tert.amide may be added. Examples of a tert.amine can be 2,2'-bipyridine or N,N,N', N'-tetramethylethyleneamine. Examples of a tert.amide can be hexamethyl phosphoric triamide.

A preferred oxidatively acting metal salt or metal salt complex is $FeCl_3$, especially in the amount of about 1.0 to 2.0 equivalents (eq).

Preferred organic solvents are ethers, preferably tetrahydrofuran.

This invention is in particular drawn to the above process when the compound of formula 1a is reacted with a compound of formula b1. In a preferred such process, $R^9$ and $R^{10}$ are isopropyl and W is lithium in the compound of formula b1 (i.e. lithium diisopropylamide). A preferred amount of this compound is about 1.0 to 1.5 eq.

This invention is also particularly drawn to the above process wherein the compound of formula 1a is reacted with a compound of formula b2. In a preferred such process, $R^{11}$ and $R^{12}$ are methyl, $R^{13}$ and $R^{14}$ are hydrogen, and W is lithium in the compound of formula b2 (i.e. lithium tetramethylpiperidide). A preferred amount of this compound is about 1.0 to 1.5 eq.

In a preferred compound 1a $R^1$ is methoxy, $R^2$ and $R^3$ are hydrogen or methoxy and $R^4$ is phenyl or phenyl substituted with methoxy.

This invention is also directed to a process for the manufacture of compounds of formula 1

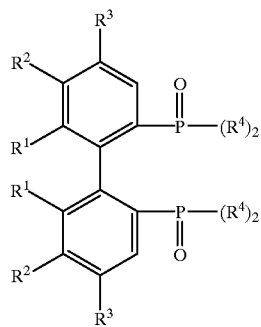

wherein
- $R^1$ and $R^2$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; or
- $R^1$ and $R^2$ together signify a fused benzene ring, a fused substituted benzene ring, a tetramethylene, trimethylene, methylenedioxy or ethylendioxy group or a system of formula a

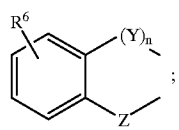

- $R^3$, and $R^6$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;
- $R^4$ signifies phenyl, substituted phenyl, naphthyl, substituted naphthyl, heteroaryl, or substituted heteroaryl;
- Y signifies $CR^7R^8$, O, S or N-$C_{1-8}$-alkyl;
- Z signifies O, S, SO or $SO_2$;
- n signifies 0 or 1;
- $R^7, R^8$ each independently signify hydrogen or $C_{1-8}$-alkyl; with the proviso that $R^4$ is not phenyl when $R^1$ and $R^2$ together signify methylenedioxy;

in which a compound of formula Ia

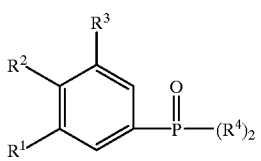

wherein
$R^1, R^2, R^3$, and $R^4$ have the significances set forth above is reacted with a $C_{1-8}$ alkyllithium or aryllithium; and an oxidatively-acting metal salt or metal salt complex is added to the resulting suspension to provide a compound of formula 1.

Preferred alkyl or aryl lithiums are tert-butyllithium or phenyllithium.

Preferred organic solvents are ethers, preferably tetrahydrofuran.

A preferred oxidatively acting metal salt or metal salt complex is $FeCl_3$, especially in the amount of about 1.0 to 2.0 equivalents (eq).

In a preferred compound 1a $R^1$ is methoxy, $R^2$ and $R^3$ are hydrogen or methoxy and $R^4$ is phenyl or phenyl substituted with methoxy.

This invention is further directed to a process for the manufacture of compounds of formula 11

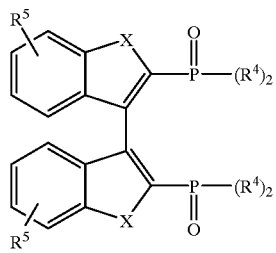

wherein
- X signifies O or S;
- $R^4$ signifies $C_{1-8}$-alkoxy, phenyloxy, substituted phenyloxy, $C_{1-8}$-alkyl, or $C_{3-7}$-cycloalkyl, phenyl, substituted phenyl, naphthyl, substituted naphthyl, heteroaryl, or substituted heteroaryl;
- $R^5$ signifies hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;

in which a compound of formula 11a

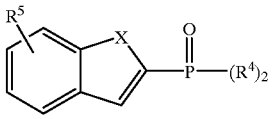

wherein
- $R^5$ and X have the significances set forth above and
- $R^4$ signifies $C_{1-8}$-alkoxy, phenyloxy, or substituted phenyloxy, phenyl, substituted phenyl, naphthyl, substituted naphthyl, heteroaryl, or substituted heteroaryl;

is reacted with a compound of formula b1 or b2 in an organic solvent

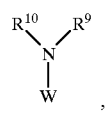

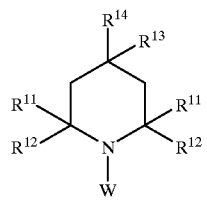

wherein
$R^9$ signifies $C_{1-8}$-alkyl, $C_{3-6}$-cycloalkyl or phenyl;

$R^{10}$ signifies $C_{1-8}$-alkyl or $C_{3-6}$-cycloalkyl;

$R^{11}$ and $R^{12}$ signify the same or different $C_{1-8}$-alkyl groups;

$R^{13}$ and $R^{14}$ each independently signify hydrogen or $C_{1-8}$-alkoxy; or $R^{13}$ signifies hydrogen or $C_{1-8}$-alkyl and $R^{14}$ signifies OW; or $R^{13}$ and $R^{14}$ together signify ketal groupings of formulae c–e

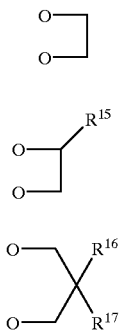

$R^{15}$ signifies $C_{1-8}$-alkyl;

$R^{16}$ and $R^{17}$ signify hydrogen or the same or different $C_{1-8}$-alkyl groups; and W signifies lithium, Mg chloride, bromide, or iodide, or magnesium amide; and an oxidatively-acting metal salt or metal salt complex is added to the resulting suspension to provide a compound of formula 1.

In a preferred such process, the amount of the compound of formula b1 or b2 is 0.5 to 3.0 eq., especially 0.9 to 1.2 eq. In another preferred process, a catalytic amount i.e. 1 to 50 mol %, preferably 5 to 20 mol % of the compound of formula b1 or b2, preferably is used in the presence of $C_{1-8}$ alkyllithium or aryllithium (such as tert-butyllithium or phenyllithium. A tert. amine or tert.amide may be added. Examples of a tert.amine can be 2,2'-bipyridine, N,N,N',N'-tetramethylethylene diamine. Examples of a tert.amide can be hexamethylphosphoric triamide.

A preferred oxidatively acting metal salt or metal salt complex is FeCl$_3$, especially in the amount of about 1.0 to 2.0 equivalents (eq).

Preferred organic solvents are ethers, preferably tetrahydrofuran.

This invention is in particular drawn to the above process when the compound of formula 1a is reacted with a compound of formula b1. In a preferred such process, $R^9$ and $R^{10}$ are isopropyl and W is lithium in the compound of formula b1 (i.e. lithium diisopropylamide). A preferred amount of this compound is about 1.0 to 1.5 eq.

This invention is also particularly drawn to the above process wherein the compound of formula 1a is reacted with a compound of formula b2. In a preferred such process, $R^{11}$ and $R^{12}$ are methyl, $R^{13}$ and $R^{14}$ are hydrogen, and W is lithium in the compound of formula b2 (i.e. lithium tetramethylpiperidide). A preferred amount of this compound is about 1.0 to 1.5 eq.

In a preferred compound 1a $R^4$ is phenyl or substituted phenyl, and/or $R^5$ is hydrogen and X is sulfur.

This invention is further directed to a process for the manufacture of compounds of formula 11

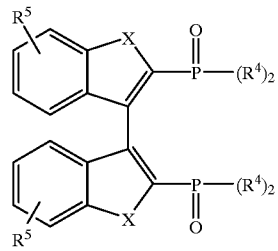

wherein

X signifies O or S;

$R^4$ signifies phenyl, substituted phenyl, naphthyl, substituted naphthyl, heteroaryl, or substituted heteroaryl; and $R^5$ signifies hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;

in which a compound of formula 11a

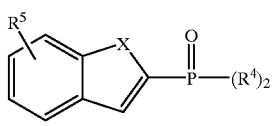

wherein $R^4$, $R^5$ and X have the significances set forth above is reacted with a $C_{1-8}$ alkyllithium or aryllithium; and an oxidatively-acting metal salt or metal salt complex is added to the resulting suspension to provide a compound of formula 1.

Preferred alkyl or aryl lithiums are tert-butyllithium or phenyllithium.

Preferred organic solvents are ethers, preferably tetrahydrofuran.

A preferred oxidatively acting metal salt or metal salt complex is FeCl$_3$, especially in the amount of about 1.0 to 2.0 equivalents (eq).

In a preferred compound 1a $R^4$ is phenyl or substituted phenyl, and/or $R^5$ is hydrogen and X is methoxy.

The term "halogen" embraces as a substituent fluorine, bromine, chlorine and iodine, with chlorine, bromine or iodine being preferred.

The term "$C_{1-8}$-alkyl" signifies in the scope of the present invention hydrocarbons with 1 to 8 carbon atoms, i.e. straight-chain or branched alkyl groups such as, for example, methyl, ethyl, propyl, isopropyl, butyl, isobutyl, tert.butyl, pentyl, isopentyl, neopentyl, hexyl, isohexyl, tert.hexyl, heptyl and octyl.

The term "$C_{3-7}$ cycloalkyl" signifies a saturated hydrocarbon ring with 3 to 7 carbon atoms, for example cyclopropyl, cyclobutyl, cyclopentyl, cyclohexyl, and cyclohexyl.

The term "$C_{1-8}$-alkoxy" signifies a $C_{1-8}$-alkyl group as defined above which is bonded via an oxygen atom. Methoxy, ethoxy, n-propoxy, isopropoxy, n-butoxy and the like can be mentioned by way of example.

The term "di-$C_{1-8}$-alkylamino" signifies an amine substituted with two $C_{1-8}$ alkyl groups which may be the same or different or which may form a ring such as pyrrolidine, piperidine or morpholine.

The term "substituted phenyl", "substituted phenyloxy" or "substituted naphthyl" signifies in the scope of the present invention mono- or also multiply-substituted phenyl, phenoxy or naphthyl.

The term "substituted benzyloxy" signifies substituted phenylmethyloxy.

The term "fused substituted benzene ring" signifies a fused benzene ring which can carry one or more substituents and is fused to one or both of rings of the compound of formula 1 as depicted above.

Suitable substituents for the phenyl, phenoxy, naphthyl or benzyloxy residue as well as for the fused benzene ring are halogen, $C_{1-8}$-alkyl, preferably methyl, $C_{1-8}$-alkoxy, preferably methoxy, di-$C_{1-8}$-alkylamino, preferably dimethylamino, trialkylsilyl, preferably trimethylsilyl, sulphamoyl, N,N-dimethylaminosulphamoyl and the like.

The term "heteroaryl" signifies in the scope of the present invention residues of 5- and/or 6-membered aromatics having one or two hetero atoms from the group of nitrogen, oxygen and sulphur. Heteroaromatics having a fused benzene ring are likewise included. Pyridine, pyrimidine, quinoline, furan, benzofuran, thiophene, pyrrole and the like can be mentioned by way of example.

The term "substituted heteroaryl" signifies in the scope of the present invention heteroaryls which are mono- or multiply-substituted by $C_{1-8}$-alkyl or $C_{1-8}$-alkoxy.

Suitable organic solvents are ethers, preferably tetrahydrofuran.

The term "$C_{1-8}$-alkyllithium" preferably signifies butyllithium or sec.butyllithium, and the term "aryllithium" preferably signifies phenyllithium.

The term "oxidatively-acting metal salt or metal salt complex" signifies in the scope of the present invention salts of transition metals such as e.g. vanadium, chromium, manganese, iron, cobalt, nickel, copper, silver, gold, ruthenium or molybdenum or complexes of the said salts with complex ligands, e.g. with solvents. As salts there come into consideration the usual salts, e.g. halides such as chlorides, bromides and iodides; carboxylates such as e.g. acetates, acetylacetonates and the like. Fe(III) acetylacetonate, $FeCl_3 \times THF$, $FeCl_3 \times 2DMSO$, $[Fe(DMF)_6]Cl_2$, $[FeCl_4^{-1}$ $_{NEt_4}^+$, $CuCl_2$, $Li_2CuCl_4$ can be mentioned by way of example. Fe (III) salts and Cu (II) salts are preferred metal salts. $FeCl_3$ is especially preferred.

The Li compounds of formula b1 or b2 can be prepared according to known processes, for example by placing a dialkylamine or tetraalkylpiperidine in an organic solvent such as e.g. tetrahydrofuran in a suitable reaction vessel under a protective gas atmosphere (e.g. in argon) and adding dropwise an alkyllithium solution, for example butyllithium in hexane, while cooling at a temperature lower than 0° C. The thus-obtained lithium dialkylamide or lithium tetraalkylpiperidide solution is used in stage a) of the process in accordance with the invention.

The Mg compounds of formula b1 or b2 can be prepared analogously, with an alkylmagnesium halide solution, for example methyl- or ethyl-magnesium bromide solution, being used in place of the alkyllithium solution. The reaction is effected at 0–65° C.

The Mg-organic compounds can also be prepared by trans-metallation of the Li-organic compounds, for example with magnesium dibromide. The Mg-organic compounds in which W signifies magnesium amide can be prepared from a dialkylamine or tetraalkylpiperidine by reaction with a dialkylmagnesium solution, for example dibutylmagnesium in an organic solvent, for example tetrahydrofuran, at about 0–65° C.

The compounds of formula Ia can be prepared according to generally known procedures, for example by dissolving a compound of formula Ia$_a$

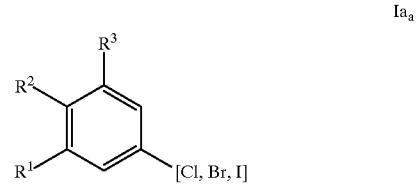

wherein $R^1$, $R^2$ and $R^3$ have the significance given above, in tetrahydrofuran and under a protective gas atmosphere (for example argon) adding the solution to a suspension of magnesium in tetrahydrofuran or reacting it with a butyllithium solution in hexane. After addition of Cl—P(—$R^4$)$_2$, wherein $R^4$ has the significance given above, and subsequent oxidation with $H_2O_2$ there is obtained a compound of formula Ia.

In place of Cl—P(—$R^4$)$_2$ there can also be used Cl—P (O)(—$R^4$)$_2$ with the oxidation being superfluous in this case. The reaction with Cl—P(O)(—$R^4$)$_2$ is preferably carried out when $R^4$ is $C_{1-8}$-alkoxy or phenoxy.

For the manufacture of compounds of formula I in which $R^4$ is $C_{1-8}$-alkoxy, compounds of formula Ia$_a$ can also be reacted directly with P(O-$C_{1-8}$-alkyl)$_3$ in the presence of catalytic amounts of Pd or Ni salts or their complexes, for example in the presence of $PdCl_2$ or $NiCl_2$.

The compounds of formula Ib are also prepared according to known processes, for example by adding dropwise benzothiophene or a substituted benzothiophene in tetrahydrofuran to a butyllithium solution in hexane at −70° C. to −10° C. Reaction with Cl—P(—$R^4$)$_2$ and oxidation with $H_2O_2$ gives a compound of formula Ib. Also, the compounds of formula Ib can be prepared by reaction with Cl—P(O)(— $R^4$)$_2$ or P(O-$C_{1-8}$-alkyl)$_3$ analogously to the preparation of the compounds of formula Ia.

The phosphorus compounds of formula I and II can be present not only in racemic form, but also in optically active form.

The racemate resolution of a compound of formula I or II which is present in the (RS) form can be carried out in a known manner, e.g. using (−)- or (+)-O,O'-dibenzoyltartaric acid (DBT) or (−)- or (+)-O,O'-di-p-tolyltartaric acid (DTT). This is conveniently effected in an inert organic solvent and at a temperature of about 0° C. to about 60° C. Solvents which can be mentioned here are especially chloroform, methylene chloride, ethyl acetate, isopropyl acetate, acetone, alcohols such as methanol or ethanol and the like, as well as also mixtures thereof.

The thus-obtained adducts of compounds of formula I or II with (−)- or (+)-DBT or DTT can subsequently be treated with an inorganic base, with the respective (R) or (S) form of the compounds of formula I or II being liberated.

The racemate resolution is described, for example, in Helvetica Chimica Acta Vol. 74 (1991) p.370 et seq.

Bisphosphonate compounds of formula I or II, that is compounds in which $R^4$ signifies $C_{1-8}$-alkoxy, are firstly converted into corresponding bis(phosphonic acid dichloride), e.g. by reaction with $SOCl_2$, and then reacted with a phenyl-, substituted phenyl-, naphthyl-, substituted naphthyl-, heteroaryl-, substituted heteroaryl-, $C_{1-8}$-alkyl- or $C_{3-7}$-cycloalkyl-Grignard compound, for example with phenylmagnesium chloride, or with a lithium compound, with the corresponding bisphosphine oxide being obtained. The reaction can be carried before or after the racemate resolution, but is preferably carried out after the racemate resolution.

Compounds of formulae I and II are valuable intermediates in the production of diphosphine ligands. These are in turn valuable building bricks of complexes with transition metals, especially with metals of Group VIII, such as, for example, ruthenium, rhodium or iridium, which are useful as catalysts in, inter alia, asymmetric hydrogenations. Complexes of diphosphine ligands with transition metals as well as their use for asymmetric hydrogenations are known and are described, for example, in U.S. Pat. No. 5,430,191.

The reduction of a bisphosphine oxide compound of formula I or II which is present in racemic or in (R) or (S) form and in which $R^4$ signifies $C_{1-8}$-alkyl, $C_{3-7}$-cycloalkyl, phenyl, substituted phenyl, naphthyl, substituted naphthyl, heteroaryl or substituted heteroaryl can be carried out in a manner known per se, such as, for example, as described in Helvetica Chimica Acta Vol. 74 (1991) p. 370 et seq. This can be effected, for example, using silanes, such as e.g. trichlorosilane, in an aromatic hydrocarbon, such as, for example, in boiling xylene, or also in acetonitrile etc., conveniently in the presence of an adjuvant base such as, for example, triethylamine, or preferably tributylamine. If desired, this reduction can be carried out in an autoclave under pressure.

The following Examples illustrate the invention and in no manner represent a limitation thereof. In these Examples the abbreviations used have the following significance:

| | |
|---|---|
| TLC | thin layer chromatography |
| HPLC | high pressure liquid chromatography |
| NMR | nuclear resonance spectroscopy |
| RV | rotation evaporator |
| RT | room temperature |
| HV | high vacuum: 0.1 mbar |
| GC | capillary gas chromatography |
| e.e. | enantiomeric excess |
| MeOBIPHEP | (6,6'-dimethoxybiphenyl-2,2'-diyl)bis(diphenyl-phosphine) |
| MeOBIPHEPO | (6,6'-dimethoxybiphenyl-2,2'-diyl)bis(diphenyl-phosphine oxide) |
| DiMeOBIPHEPO | (5,5',6,6'-tetramethoxybi-phenyl-2,2'-diyl)bis(diphenyl-phosphine oxide) |
| TriMeOBIPHEPO | (4,4',5,5',6,6'-hexamethoxy-biphenyl-2,2'-diyl)bis(di-phenylphosphine oxide) |
| all-MeOBIPHEPO | (4,4',5,5',6,6'-hexamethoxy-biphenyl-2,2'-diyl)bis[bis(3,4,5-trimethoxyphenyl)phosphine oxide] |
| BITIANPO | 2,2'-bis(diphenylphosphinoyl)-3,3'-bibenzo[b]thiophene |
| Fe(acac) | iron (III) acetylacetonate |
| All temperatures are given in degrees Celsius. | |

EXAMPLE 1

Manufacture of a compound of formula I in which $R^1$ signifies methoxy, $R^2$ and $R^3$ signify hydrogen and $R^4$ signifies phenyl (MEOBIPHEPO).

a) 36.8 g (1.596 mol) of magnesium were suspended in 200 ml of tetrahydrofuran under argon in a 4.5 l four-necked flask provided with a condenser, thermometer, mechanical stirrer and dropping funnel with pressure compensation. A solution of 298.0 g (1.593 mol) of 3-bromoanisole in 400 ml of tetrahydrofuran was added dropwise to the suspension within 1.75 h. while stirring vigorously, with the temperature being held at 45–55° C. After completion of the dropwise addition the resulting grey solution was stirred at 40–45° C. for a further 1 h. The reaction solution was cooled to about 10° C. by means of an ice bath and treated dropwise within 1 h. with a solution of 362 g (1.641 mol) of P-chlorodiphenylphosphine in 400 ml of tetrahydrofuran. In so doing the temperature was held at 25–30° C. by means of an ice-water bath. After an additional stirring period of 1 h. at about 25° C. the reaction mixture was cooled to 10° C. by means of an ice bath. Subsequently, 400 ml of deionized water were added rapidly thereto from a dropping funnel while stirring vigorously, with the temperature rising to a max. of 35° C. 180.0 g (1.587 mol) of 30% hydrogen peroxide solution were added dropwise to the turbid yellowish solution within 45 min., with the reaction temperature being held at 25–30° C. by cooling. Shortly after completion of the dropwise addition of the hydrogen peroxide the reaction had finished according to TLC. The resulting clear yellow solution was treated at 25° C. with 100 ml of saturated $Na_2SO_3$ solution, following which peroxide could no longer be detected in the reaction mixture. The aqueous phase of the reaction mixture was separated and back-extracted with 300 ml of heptane. The combined organic phases were washed with 500 ml of saturated NaCl solution and dried over magnesium sulphate, filtered and evaporated on a RV. The residue (459.6 g, 93.6%) was dissolved in 800 ml of toluene at 70° C., treated with 800 ml of heptane and cooled slowly to RT. In so doing crystallization started and was subsequently completed at 0° C. during 1 h. The mother liquor was removed by decantation. The crystallizate was again digested with 300 ml of heptane at 50° C. for a short time and left at 0° C. for 1 h. Subsequently, the white crystals were filtered off under suction and washed three times with 100 ml of heptane each time and dried at 80° C. in a HV for 3 h.

The yield was 448.3 g (88.8%) of (3-methoxyphenyl) diphenylphosphine oxide.

b) 40 g (0.395 mol) of diisopropylamine as well as 250 ml of tetrahydrofuran were placed under argon in a 2.5 l four-necked flask provided with a condenser, thermometer, mechanical stirrer and dropping funnel with pressure compensation. After cooling to −18° C. 220 ml (0.352 mol) of butyllithium solution in hexane were added dropwise within 30 min. while stirring, with the temperature being held below −15° C. The reaction mixture was stirred at −20° C. for a further 1 h. To the resulting lithium diisopropylamide solution was added dropwise within 30 min. a solution of 100 g (0.316 mol) of (3-methoxyphenyl)diphenylphosphine oxide in 350 ml of tetrahydrofuran, with the temperature being held below −15° C. After an additional period of 1 h. at −20° C. a suspension, pre-cooled to −15° C., consisting of 72.5 g (0.447 mol) of iron(III) chloride (anhydrous) in 400 ml of tetrahydrofuran was added directly. After an additional stirring period of 1 h., without cooling the reaction mixture was concentrated at 70° C./15 mbar. The dark brown oily residue was taken up in 1000 ml of methylene chloride. The solution was cooled in an ice bath and treated dropwise with 75 ml (1.0 mol) of 25% ammonium hydroxide solution while stirring vigorously, with the temperature being held below 15° C. After an additional stirring period of 1 h. at RT the suspension of iron salts obtained was left to stand for 16 h. Then, it was filtered and the filter residue was rinsed with 1000 ml of methylene chloride. The brownish filtrate was concentrated to about 10° C. of the original volume at 50° C. and 600 mbar and treated with 150 ml of methanol. During the evaporation of the methylene chloride on a RV crystallization set in and was completed at RT over 16 h. The crystals were filtered off on a suction filter, washed 3 times with 50 ml of methanol and dried in a HV at 140° C. for 1 h. Yield: 82.8 g (85.3%) of (RS)-MeOBIPHEPO as a white powder; HPLC content 100%.

c) 7.87 g (77.7 mmol) of diisopropylamine as well as 50 ml of tetrahydrofuran were placed under argon in a 1.5 l four-necked flask provided with a condenser, thermometer, mechanical stirrer and dropping funnel with pressure compensation. After cooling to −60° C. 43 ml (30.9 mmol) of 1.6M butyllithium solution in hexane were added dropwise within 5 min. while stirring. The reaction mixture was stirred at −55° C. for a further 15 min. To the resulting lithium diisopropylamide solution was added dropwise a solution of 20 g (64.2 mmol) of (3-methoxyphenyl)diphenylphosphine oxide in 80 ml of tetrahydrofuran, with the temperature being held below −70° C. After an additional stirring period of 2 h. at −70° C. a solution of 31.7 g (89.8 mmol) of iron(III) acetylacetonate was added in one portion, with the temperature rising to −60° C. After an additional stirring period of 16 h. at RT the reaction mixture was concentrated on a RV and the residue was taken up in 1000 ml of methylene chloride. The solution obtained was washed in sequence 5 times with 40 ml of 2N hydrochloric acid, 50 ml of 25% ammonium hydroxide solution, 50 ml of 3N sodium hydroxide solution and finally twice with 200 ml of deionized water and dried over sodium sulphate, filtered and evaporated to dryness. The oily residue (26 g) contained 35% of (RS)-MeOBIPHEPO and 31% of starting material. Yield: 46%.

d) Analogously to 1c), 12.5 g (93 mmol) of copper(II) chloride in solid form were used as the oxidation agent in place of Fe(acac)$_3$. There were isolated 21 g of a brown oil which contained 15% (RS)-MeOBIPHEPO.

EXAMPLE 2

Manufacture of a compound of formula I in which $R^1$ and $R^2$ signify methoxy, $R^3$ signifies hydrogen and $R^4$ signifies phenyl (DiMeOBIPHEPO).

3.5 g (34.6 mmol) of diisopropylamine as well as 23 ml of tetrahydrofuran were placed under argon in a 500 ml four-necked sulphonation flask having a thermometer, mechanical stirrer and 250 ml dropping funnel with pressure compensation. After cooling to −16° C. 19 ml (30.4 mmol) of 1.6M butyllithium solution in hexane were added dropwise within 2 min. The reaction mixture was stirred at −18° C. for a further 15 min. To this lithium diisopropylamide solution was added dropwise a solution of 10 g (28.8 mmol) of (3,4-dimethoxyphenyl) diphenylphosphine oxide in 100 ml of tetrahydrofuran, with the temperature being held below −15° C. After an additional stirring period of 1.5 h. at −17° C. 6.5 g (40.1 mmol) of iron(III) chloride (anhydrous) were added in one portion to the beige suspension, with the temperature rising to 11° C. After an additional stirring period of 16 h. at RT the reaction mixture was concentrated on a RV in a vacuum at 60° C. The residue was taken up in 200 ml of methylene chloride and 40 ml of 2N hydrochloric acid. After carrying out the extraction the organic phase was separated, dried over magnesium sulphate, filtered and then evaporated to dryness on a RV. The dark brown residue (11.1 g) was filtered over 300 g of silica gel with methylene chloride/methanol (5 to 15% methanol). The eluate (1$^{st}$ fraction) was evaporated on a RV and the residue (9.8 g) was dissolved in 100 ml of methanol at 65–70° C. 100 ml of deionized water were added dropwise to this solution at RT, with crystallization setting in. The crystallization was completed at 4° C. overnight. The crystals were filtered off and washed 3 times with 10 ml of water/ethanol (2:1) and dried at 90° C. in a HV for 6 h. The yield was 7.5 g (77%) of (RS)-(5,5',6,6'-tetramethoxybiphenyl-2,2'-diyl)bis(diphenylphosphine oxide).

EXAMPLE 3

Manufacture of a compound of formula I in which $R^1$, $R^2$ and $R^3$ signify methoxy and $R^4$ signifies phenyl (TriMeOBIPHEPO).

3.4 g (33.8 mmol) of diisopropylamine as well as 22 ml of tetrahydrofuran were placed under argon in a 250 ml four-necked sulphonation flask having a thermometer, mechanical stirrer and 100 ml dropping funnel with pressure compensation. After cooling to −20° C. 18 ml (28.8 mmol) of 1.6M butyllithium solution in hexane were added dropwise within 5 min. The reaction mixture was stirred at −20° C. for a further 15 min. To this lithium diisopropylamide solution was added dropwise a solution of 10 g (27 mmol) of (3,4,5-trimethoxyphenyl) diphenylphosphine oxide in 60 ml of tetrahydrofuran, with the temperature being held below −15° C. After an additional stirring period of 1 h. at −20° C. 6.3 g (38.9 mmol) of iron(III) chloride (anhydrous) were added in one portion to the dark brown solution, with the temperature rising to 20° C. After an additional stirring period of 16 h. at RT the reaction mixture was concentrated on a RV in a vacuum at 60° C. The residue was taken up in 100 ml of methylene chloride. 6 ml of 25% ammonium hydroxide solution and 6 g of magnesium sulphate were added to the resulting solution while stirring vigorously. After an additional stirring period of 15 min. the brown precipitate was filtered off and washed with about 50 ml of methylene chloride. The filtrate was evaporated to dryness on a RV and filtered over 50 g of silica gel with toluene/diethyl ether/methanol (7/2/1). After evaporation of the solvent the residue was dissolved in methylene chloride and treated with toluene. The solution was concentrated on a RV, with crystallization setting in. The crystallizate was filtered off under suction, washed with toluene and dried in a HV. The yield was 6.5 g (65%) of (RS)-(4,4',5,5',6,6'-hexamethoxybiphenyl-2,2'-diyl)bis(diphenylphosphine oxide).

EXAMPLE 4

Manufacture of a compound of formula I in which $R^1$ signifies methoxy, $R^2$ and $R^3$ signify hydrogen and $R^4$ signifies ethoxy.

a) 6.6 g (47 mmol) of 2,2,6,6-tetramethylpiperidine as well as 30 ml of tetrahydrofuran were placed under argon in a 500 ml four-necked sulphonation flask having a thermometer, mechanical stirrer and 100 ml dropping funnel with pressure compensation. After cooling to −17° C. 27 ml (43.2 mmol) of 1.6M butyllithium solution in hexane were added dropwise within 2 min. The reaction mixture was stirred at −17° C. for a further 15 min. To this lithium tetramethylpiperidide solution was added dropwise a solution of 10 g (40.8 mmol) of diethyl 3-methoxyphenylphosphonate in 40 ml in tetrahydrofuran, with the temperature being held below −15° C. After an additional stirring period of 1.5 h. at −20° C. 8.6 g (53 mmol) of iron(III) chloride (anhydrous) were added in one portion to the dark brown reaction solution, with the temperature rising to 10° C. After an additional stirring period of 16 h. at RT the reaction mixture was concentrated on a RV in a vacuum at 60° C. The residue was taken up in 100 ml of methylene chloride and washed 3 times with 50 ml of 2N hydrochloric acid, dried over magnesium sulphate, filtered (sic) and then evaporated to dryness on a RV. The residue (7.8 g) was dissolved in 30 ml of tert-butyl methyl ether and diluted with 20 ml of hexane, with crystallization setting in. The crystallizate was filtered off under suction, washed with hexane and dried in a HV. The yield was 4.1 g (41%) of (RS)-(6,6'-dimethoxybiphenyl-2,2'-diyl)bis(phosphonic acid diethyl ester). M.p.: 146.8° C.

b) 36 ml (46.8 mmol) of 1.3M sec.-butyllithium solution in cyclohexane were added dropwise to a solution of 10 g (40.8 mmol) of diethyl 3-methoxyphenylphosphonate in 17.6 ml (117 mmol) of N,N,N',N'-tetramethyldiamine and 0.06 ml (0.42 mmol) of diisopropylamine in 50 ml of tetrahydrofuran in a 250 ml four-necked sulphonation flask having a thermometer, mechanical stirrer and 100 ml dropping funnel with pressure compensation, with the temperature being held at −65° C. After an additional stirring period of 1.5 h. 8.6 g (53 mmol) of iron(III) chloride (anhydrous) were added in one portion to the orange coloured, milky reaction mixture, with the temperature rising to 5° C. After an additional stirring period of 16 h. at RT the reaction mixture was worked up as under 4 a). The yield was 5.5 g (55%) of (RS)-(6,6'-dimethoxybiphenyl-2,2'-diyl)bis (phosphonic acid diethyl ester). M.p.: 146° C.

EXAMPLE 5

Manufacture of a compound of formula I in which $R^1$, $R^2$ and $R^3$ signify methoxy and $R^4$ signifies phenyl trisubstituted by methoxy, and subsequent racemate resolution (all-MEOBIPHEPO).

a) 85 g (0.344 mol) of 3,4,5-trimethoxybromobenzene were added dropwise under argon in 40 min. in such a manner that the temperature did not rise above 35° C. to a suspension consisting of 9.2 g (0.378 mol) of magnesium in 50 ml of tetrahydrofuran in a 750 ml four-necked sulphonation flask having a thermometer, mechanical stirrer and 250 ml dropping funnel with pressure compensation. The resulting grey solution was stirred at 35° C. for a further 1 h. After cooling to 10° C. 14.2 g (0.115 mol) of phosphorus trichloride in 50 ml of tetrahydrofuran were added dropwise within 50 min. in such a manner that the reaction temperature did not exceed 15° C. The grey suspension was stirred at RT overnight and then treated with 100 ml of saturated ammonium chloride solution, with the temperature rising to a maximum of 40° C. The phases were separated and the organic phase was washed twice with 400 ml of deionized water. The aqueous phases were combined and re-extracted with 300 ml of ethyl acetate. The combined organic phases were washed with 300 ml of saturated sodium chloride solution, dried over magnesium sulphate, filtered and evaporated on a RV at 50° C. The yellowish, oily residue was treated with 150 ml of ethanol at RT while stirring, with crystallization setting in. After stirring at 0° C. for 30 min. the crystalline material was filtered off under suction, washed three times with 30 ml of ethanol and dried for 2 h. at 80° C. in a HV.

The yield was 31.6 g (52%) of tris(3,4,5-trimethoxyphenylphosphine); m.p. 130–135° C.

b) 31.6 g (59.3 mmol) of tris(3,4,5-trimethoxyphenyl)phosphine were dissolved in a mixture of 100 ml of methylene chloride and 150 ml of ethanol in a 500 ml four-necked sulphonation flask having a thermometer, mechanical stirrer, 100 ml dropping funnel and condenser. 6.8 g (60 mmol) of 30% hydrogen peroxide were added dropwise to the resulting solution within 15 min., with the reaction temperature being held at 15–20° C. Shortly after completion of the dropwise addition of hydrogen peroxide the reaction had finished according to TLC. The reaction solution obtained was treated with 5 ml of saturated sodium sulphite solution, following which peroxide could no longer be detected in the reaction mixture. The reaction mixture was treated with 200 ml of methylene chloride and extracted twice with 300 ml of deionized water. The combined phases were re-extracted with 300 ml of methylene chloride, washed with 300 ml of saturated sodium chloride solution, dried over magnesium sulphate, filtered and treated with 200 ml of hexane. The solution obtained was concentrated on a RV at 50° C./600 mbar, with crystallization setting in. After stirring at 0° C. for 2 h. the crystalline material was filtered off under suction, washed twice with 50 ml of hexane and dried for 2 h. at 100° C. in a HV. 13.0 g of tris(3,4,5-trimethoxyphenyl)phosphine oxide were isolated at a first crystallizate. A further 12.7 g of tris(3,4,5-trimethoxyphenyl)phosphine oxide were obtained from the mother liquor as a second crystallizate. Both crystallizates were identical and uniform. The total yield of tris(3,4,5-trimethoxyphenyl)phosphine oxide was 25.7 g (79%).

c) 4.1 g (28.9 mmol) of diisopropylamine in 80 ml of tetrahydrofuran were placed at −20° C. in a 350 ml four-necked flask having a condenser, mechanical stirrer, 100 ml dropping funnel with pressure compensation and a head-piece for argon gasification. 16 ml (25.6 mmol) of 1.6M butyllithium solution in hexane were added dropwise while stirring with 10 min. The reaction mixture was stirred at −20° C. for a further 15 min. To the resulting lithium diisopropylamide solution were added portionwise 12.7 g (23.2 mmol) of tris(3,4,5-trimethoxyphenyl)phosphine oxide at −20° C. To the resulting dark red reaction solution was added a solution of 5.34 g (32.9 mmol) of iron(III) chloride (anhydrous) in 20 ml of toluene and 10 ml of tetrahydrofuran. After the addition the reaction solution was left to warm to RT while stirring. Then, the reaction mixture was evaporated on a RV at 60° C. The dark, oily residue was taken up in 200 ml of methylene chloride, and, after cooling to 0° C., treated with 6 ml (80 mmol) of 25% ammonium hydroxide solution. After stirring at 0° C. for 30 min. the iron salts were filtered off and rinsed with 100 ml of methylene chloride. The filtrate was dried over magnesium sulphate, filtered and evaporated. 15.3 g of crude product were obtained as a dark oil. A second reaction carried out in the same manner under identical conditions gave a further 14.9 g of crude product. Both crude products were chromatographed together on 200 g of silica gel with ethyl acetate/ethanol (9/1 to 1/1) as the eluent. After evaporation of the solvent and drying in a high vacuum there were obtained 2.4 g of pre-purified product as a colourless resien. According to NMR the material contained 72% of (RS)-(4,4',5,5',6,6'-hexamethoxybiphenyl-2,2'-diyl)bis[bis(3,4,5-trimethoxyphenyl)]phosphine oxide and 28% of tris(3,4,5-trimethoxyphenyl)-phosphine oxide.

d) 24 g (17.3 mmol) of (RS)-(4,4',5,5',6,6'-hexamethoxybiphenyl-2,2'-diyl)bis[bis(3,4,5-trimethoxyphenyl)]phosphine oxide, which still contained 28% tris(3,4,5-trimethoxyphenyl)]phosphine oxide, and 11 g (30.7 mmol) of (−)-O,O'-dibenzoyl-L-tartaric acid were heated together under reflux for a short period in 40 ml of ethyl acetate in a 250 ml round flask having a condenser, 2 separating funnels and a magnetic stirrer. The mixture was left to cool to RT overnight while stirring. The white crystallizate was filtered off under suction, washed with 10 ml of ethyl acetate and dried in a HV at RT for 1 h. There were obtained 9 g of (S)-(4,4',5,5',6,6'-hexamethoxybiphenyl-2,2'-diyl)bis[bis-(3,4,5-trimethoxyphenyl)]phosphine oxide/(−)-DBT adduct.

da) 9 g of (S)-(4,4',5,5',6,6'-hexamethoxybiphenyl-2.2'-diyl)bis[bis-(3,4,5-trimethoxyphenyl)]phosphine oxide/(−)-DBT adduct were treated while stirring in 50 ml of ethyl acetate with a solution of 1 g (10 mmol) of sodium carbonate in 50 ml of deionized water. The two phases were separated and the aqueous phase was extracted with 20 ml of ethyl acetate. The combined organic phases were washed with 50 ml of deionized water, dried over magnesium sulphate, filtered, concentrated to dryness on a RV and dried in a HV at RT for 1 h. The yield of (S)-(4,4',5,5',6,6'- hexamethoxybiphenyl-2,2'-diyl)bis[bis(3,4,5-trimethoxyphenyl)]phosphine oxide was 5.9 g (68% of theory based on the (RS) compound).

e) The mother liquor of the (S)-(4,4',5,5',6,6'-hexamethoxybiphenyl-2,2'-diyl)bis[bis-(3,4,5-trimethoxyphenyl)]phosphine oxide/(−)-DBT adduct was treated with a solution of 5 g (47 mmol) of sodium carbonate in 50 ml of deionized water in a 500 ml round flask having a condenser and magnetic stirrer. The two phases were separated and the aqueous phase was extracted with 50 ml of methyl acetate. The combined organic phases were washed with a further 50 ml of deionized water, dried over magnesium sulphate, filtered off and concentrated to dryness on a RV. The residue and 11 g (30.7 mmol) of (+)-O,O'-dibenzoyl-D-tartaric acid in 40 ml of ethyl acetate were heated under reflux for a short period. The mixture was left to cool to RT overnight while stirring. The white crystallizate was filtered off under suction, washed twice with 10 ml of ethyl acetate and dried in a HV at RT for 1 h. There were obtained 8 g of (R)-(4,4',5,5', 6,6'-hexamethoxybiphenyl-2,2'-diyl)bis[bis(3,4,5-trimethoxyphenyl)]phosphine oxide/(+)-DBT adduct.

ea) 8 g of (R)-(4,4',5,5',6,6'-hexamethoxybiphenyl-2,2'-diyl)bis[bis(3,4,5-trimethoxyphenyl)]phosphine oxide/(+)-DBT adduct were treated while stirring in 50 ml of ethyl acetate with a solution of 1 g (10 mmol) of sodium carbonate in 50 ml of deionized water. The two phases were separated and the aqueous phase was extracted with 20 ml of ethyl acetate. The combined organic phases were washed with 50 ml of deionized water, dried over magnesium sulphate, filtered, concentrated to dryness on a RV and dried in a HV at RT for 1 h. The yield of (R)-(4,4',5,5',6,6'-hexamethoxybiphenyl-2,2'-diyl)bis[bis(3,4,5-trimethoxyphenyl)]phosphine oxide was 5.6 g (64% of theory based on the (RS) compound).

EXAMPLE 6

Reduction of the compound described in Example 5.

a) 30 ml of xylene (isomer mixture), 5.6 g (5.1 mmol) of (S)-(4,4',5,5',6,6'-hexamethoxybiphenyl-2,2'-diyl)bis[bis(3,4,5-trimethoxyphenyl)]phosphine oxide, 15 ml (63 mmol) of tributylamine and 5.1 ml (50 mmol) of trichlorosilane were placed at RT under argon and while stirring in a 100 ml four-necked sulphonation flask having a condenser, thermometer, magnetic stirrer, septum stopper and headpiece for argon gasification. The mixture was boiled under reflux for 8 h., cooled to 50° C. and treated with 50 ml of 30% sodium hydroxide solution. The mixture was cooled to RT, treated with 100 ml of toluene and diluted with 100 ml of deionized water. The organic phase was separated, washed twice with 100 ml of 2N sodium hydroxide solution and 3 times with 50 ml of saturated NaCl solution, dried over magnesium sulphate, filtered, concentrated and dried in a HV at 100° C. for 2 h. The residue (6 g) was filtered over 100 g of silica gel with hexane/ethyl acetate (1/1). After evaporation of the solvent and drying in a HV there was isolated (S)-(4,4',5,5',6,6'-hexamethoxybiphenyl-2,2'-diyl)bis[bis(3,4,5-trimethoxyphenyl)]phosphine. The yield of (S)-(4,4',5,5',6,6'-hexamethoxybiphenyl-2,2'-diyl)bis[bis(3,4,5-trimethoxyphenyl)]phosphine was 4.8 g (88%) as a colourless resin.

b) 30 ml of xylene (isomer mixture), 5.4 g (4.9 mmol) of (R)-(4,4',5,5',6,6'-hexamethoxybiphenyl-2,2'-diyl)bis[bis(3,4,5-trimethoxyphenyl)]phosphine oxide, 15 ml (63 mmol) of tributylamine and 5.1 ml (50 mmol) of trichlorosilane were introduced at RT under argon and while stirring into a 100 ml four-necked sulphonation flask having a condenser, thermometer, magnetic stirrer, septum stopper and headpiece for argon gasification. The mixture was boiled under reflux for 8 h., cooled to 50° C. and treated with 50 ml of 30% sodium hydroxide solution. The mixture was cooled to RT, treated with 100 ml of toluene and diluted with 100 ml of deionized water. The organic phase was separated, washed twice with 100 ml of 2N sodium hydroxide solution and 3 times with 50 ml of saturated NaCl solution, dried over magnesium sulphate, filtered, concentrated and dried in a HV at 100° C. for 2 h. The residue was filtered over 100 g of silica gel with hexane/ethyl acetate (1/1). After evaporation of the solvent and drying in a HV there was isolated (R)-(4,4',5,5',6,6'-hexamethoxybiphenyl-2,2'-diyl)bis(3,4,5-trimethoxyphenyl)phosphine. The yield of (R)(4,4',5,5',6,6'-hexamethoxybiphenyl-2,2'-diyl)bis(3,4,5-trimethoxyphenyl)phosphine was 5 g (96%) as a colourless resin.

EXAMPLE 7

Manufacture of a compound of formula II in which $R^5$ signifies hydrogen, X signifies sulphur and $R^4$ signifies phenyl (BITANPO).

a) 300 ml (0.48 mol) of 1.6M butyllithium solution in hexane to 50 ml of hexane were placed at −70° C. under argon and while stirring in a 1.5 l four-necked flask having a condenser, mechanical stirrer, thermometer and 500 ml dropping funnel with pressure compensation. 85 g (0.633 mol) of benzothiophene in 200 ml of tetrahydrofuran were added dropwise to this mixture, with the temperature rising to a maximum of −50° C. After completion of the addition the reaction solution was left to warm to −10° C. while stirring. The solution was thereupon again cooled to −70° C. and 103 g (0.467 mol) of P-chlorodiphenylphosphine were added dropwise without the temperature exceeding −55° C. Subsequently the reaction solution was stirred without cooling until RT had been reached. The reaction mixture was treated with 200 ml of saturated ammonium chloride solution. After an addition of 200 ml of deionized water and 400 ml of methylene chloride the phases were separated. The organic phase was washed twice with 100 ml of saturated sodium chloride solution, dried over magnesium sulphate, filtered and concentrated on a RV. The residue was dissolved in 350 ml of ethanol while heating to reflux and the solution was left to cool overnight. The white crystallizate was filtered off under suction, washed with 50 ml of ethanol and dried in a HV at RT for 1 h. There were obtained 105 g of crude product which, according to $^{31}$P-NMR, consisted of an about 6/1 mixture of 2-benzo[b]thiophenyldiphenylphosphine and 2-benzo[b]thiophenyl-diphenylphosphine oxide.

b) The crude product obtained in 7a) was dissolved in 200 ml of methanol and treated dropwise while stirring with 37.0 g (0.326 mol) of 30% hydrogen peroxide, with the temperature not exceeding 30° C. The clear reaction solution obtained was treated RT with 50 ml of saturated sodium sulphite solution, following which peroxide could no longer be detected in the reaction mixture. The methanol was distilled off on a RV. The aqueous residue was extracted with 200 ml of methylene chloride and the organic phase was washed with 50 ml of saturated sodium chloride solution, dried over magnesium sulphate, filtered and evaporated on a RV. The residue was dissolved in 150 ml of toluene at 70° C., treated with 150 ml of hexane and cooled slowly to RT. The crystallizate was filtered off under suction, washed with 100 ml of hexane and dried in a HV at RT for 1 h. The yield was 101 g (63%) of 2-benzo[b]thiophenyl-diphenylphosphine oxide as a white powder, m.p.: 144–145° C.

c) 11.0 g (0.108 mol) of diisopropylamine as well as 75 ml of tetrahydrofuran were placed under argon gasification in a 750 ml four-necked sulphonation flask having a thermometer, mechanical stirrer and 250 ml dropping funnel with pressure compensation.

After cooling to −18° C. 66 ml (0.105 mol) of 1.6M butyllithium solution in hexane were added dropwise, with the temperature not exceeding −15° C. The reaction mixture was stirred at −20° C. for a further 1 h. To the resulting lithium diisopropylamide solution was added dropwise a solution consisting of 33.4 g (0.1 mol) of 2-benzo[b]thiophenyldiphenylphosphine oxide in 150 ml of tetrahydrofuran, with the temperature being held below −15° C., and the mixture was stirred at −20° C. for a further hour. To this mixture was added in one portion a suspension, cooled to −15° C., of 24 g (0.145 mol) of iron(III) chloride (anhydrous) in 150 ml of tetrahydrofuran, with the temperature rising to 50° C. After an additional stirring period of 1 h. without cooling the reaction mixture was concentrated on a RV. The dark brown residue was taken up in 250 ml of methylene chloride. The solution was cooled by means of an ice bath and treated dropwise within 10 min. with 25 ml (0.33 mol) of 25% ammonium hydroxide solution. The suspension of iron salts obtained was filtered and washed with 100 ml of methylene chloride. The brownish filtrate was concentrated to about 10% of the original volume on a RV and treated with 200 ml of ethyl acetate. In so doing, crystallization set in. Upon evaporation of the residual methylene chloride on a RV crystallization became complete. The yellow crystalling material was filtered off under suction, washed with 50 ml of ethyl acetate and dried in a HV. The yield of (RS)-bis(diphenylphosphinoyl)-3,3'-bibenzo[b]thiophene was 27 g (82%).

EXAMPLE 8

Manufacture of a compound of formula II in which $R^5$ signifies hydrogen, X signifies sulphur and $R^4$ signifies ethoxy.

a) Preparation of diethyl benzo[b]thiophen-2-yl)phosphonate: 65 g of 2-bromobenzothiophene (GC purity 92%; 0.280 mol) were added to 1.5 g of palladium chloride (0.084 mol) at 25° C. under argon and while stirring well in a 50 ml four-necked sulphonation flask having a 10 cm Vigreux distillation headpiece, magnetic stirrer, thermometer, 50 ml dropping funnel with pressure compensation and headpiece for argon gasification. After heating to 160° C. 61 g of triethyl phosphite (0.367 mol) were added dropwise to this mixture within 2 h. The ethyl bromide formed was distilled off continuously in a dry ice receiver. Subsequently, the reaction solution was stirred at 160° C. for 1 h. The excess triethyl phosphite was distilled off in a water-jet vacuum. Subsequently, the diethyl (benzo[b]thiophen-2-yl)phosphonate was distilled in a high vacuum (bath 160° C., head 140° C.). Yield: 67.4 g (89%) of diethyl (benzo[b]thiophen-2-yl)phosphonate as a colourless oil.

b) Manufacture of (RS)-(3,3'-bibenz[b]thiophene-2,2'-diyl)bis(phosphonic acid diethyl ester).

71 ml of 2,2,6,6-tetramethyl-piperidine (0.418 mol) as well as 200 ml of tetrahydrofuran were placed under argon in the apparatus described under a). After cooling to −70° C. 208 ml of 1.6M butyllithium solution in hexane (0.334 mol) were added dropwise while stirring, with the temperature always being held below −50° C. The reaction mixture was stirred at −10° C. for a further 15 min. The solution was again cooled to −70° C. and 84.4 g of diethyl (benzo[b]thiophen-2-yl)phosphonate (0.299 mol) and 200 ml of tetrahydrofuran were added dropwise while stirring well, with the temperature being held below −60° C. After an additional stirring period of 2 h. at −70° C. a suspension, pre-cooled to −10° C., of 68 g of anhydrous iron(III) chloride (0.418 mol) in 200 ml of tetrahydrofuran was allowed to flow in in one portion, with the temperature rising to −45° C. After an additional stirring period of 1 h. without cooling the reaction mixture was taken up in 400 ml of 2N HCl and 600 ml of toluene. The separated organic phase was washed with 200 ml of saturated $NaHCO_3$ solution and twice with 200 ml of deionized water, dried over about 50 g of magnesium sulphate, filtered and concentrated on a RV. The residue was filtered over 200 g of Kieselgel 60 with toluene. After evaporation the residue was dissolved in 100 ml of ethyl acetate while warming and the solution was left to stand at 4° C. for 2 h. The pure crystallizate obtained was filtered off under suction, washed with about 50 ml of hexane and dried in a HV at 60° C. for 1 h. Yield: 51.6 g (64.1%) of (RS)-(3,3'-bibenzo[b]thioiphene-2,2'-diyl)bis(phosphonic acid diethyl ester) as a white powder.

What is claimed is:

1. A process for converting a monophosphonate of formula Ia

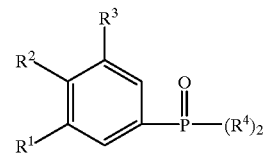

wherein $R^1$ and $R^2$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; or $R^1$ and $R^2$ together signify a fused benzene ring, a fused substituted benzene ring, a tetramethylene, trimethylene, methylenedioxo, ethylenedioxo group or a system of formula a

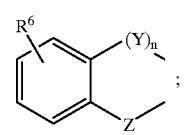

$R^3$ and $R^6$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; and $R^4$ signifies $C_{1-8}$-alkoxy, phenyloxy, substituted phenyloxy, phenyl, substituted phenyl, naphthyl, substituted naphthyl, heteroaryl, or substituted heteroaryl;

to a bisphosphonate of formula I

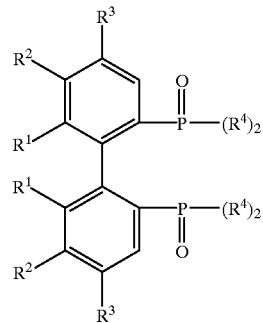

wherein
$R^1$, $R^2$ and $R^3$ are as above,
$R^4$ signifies $C_{1-8}$-alkoxy, phenyloxy, substituted phenyloxy, $C_{1-8}$-alkyl, $C_{3-7}$-cycloalkyl, phenyl, substituted phenyl, naphthyl, substituted naphthyl, heteroaryl, or substituted heteroaryl;
Y signifies $CR^7R^8$, O, S or N-$C_{1-8}$-alkyl;
Z signifies O, S, SO or $SO_2$;
n signifies 0 or 1;
$R^7$, $R^8$ each independently signify hydrogen or $C_{1-8}$-alkyl;
with the proviso that $R^4$ is not phenyl when $R^1$ and $R^2$ together signify methylenedioxy;
comprising treating said monophosphonate with a compound of formula b1 or b2

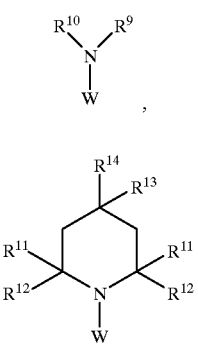

wherein
$R^9$ signifies $C_{1-8}$-alkyl, $C_{3-6}$-cycloalkyl or phenyl;
$R^{10}$ signifies $C_{1-8}$-alkyl or $C_{3-6}$-cycloalkyl;
$R^{11}$ and $R^{12}$ signify the same or different $C_{1-8}$-alkyl groups;
$R^{13}$ and $R^{14}$ each independently signify hydrogen or $C_{1-8}$-alkoxy; or
$R^{13}$ signifies hydrogen or $C_{1-8}$-alkyl and
$R^{14}$ signifies OW; or
$R^{13}$ and $R^{14}$ together signify a ketal grouping selected from the group consisting of formulae c–e

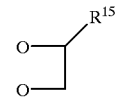

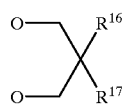

$R^{15}$ signifies $C_{1-8}$-alkyl;
$R^{16}$ and $R^{17}$ signify hydrogen or the same or different $C_{1-8}$-alkyl groups; and
W signifies lithium, magnesium chloride, bromide, or iodide, or magnesium amide;
in an organic solvent to form a suspension, and thereafter oxidizing said treated monophosphonate in the resulting suspension with an oxidatively-acting metal salt to convert said treated monophosphonate to said bisphosphonate.

2. The process of claim 1 wherein the metal in the oxidatively acting metal salt is selected from the group consisting of vanadium, chromium, manganese, iron, cobalt, nickel, copper, silver, gold, ruthenium and molybdenum.

3. A process of claim 1 wherein a 1 to 50 mol % of the compound formula b1 or b2 is used in the presence of $C_{1-8}$ alkyllithium or aryllithium.

4. A process of claim 1 wherein the oxidatively acting metal salt is $FeCl_3$.

5. A process of claim 4 wherein 1.0 to 2.0 eq. of $FeCl_3$ is used.

6. A process of claim 1 wherein the compound of formula 1a is reacted with a compound of formula b1.

7. A process of claim 1 wherein $R^9$ and $R^{10}$ are isopropyl and W is lithium in the compound of formula b1.

8. A process of claim 1 wherein the compound of formula 1a is reacted with a compound of formula b2.

9. A process of claim 8 wherein $R^{11}$ and $R^{12}$ are methyl, $R^{13}$ and $R^{14}$ are hydrogen, and W is lithium in the compound of formula b2.

10. A process of claim 1 wherein $R^4$ is phenyl or phenyl substituted with methoxy.

11. A process of claim 1 wherein $R^1$, $R^2$, and $R^3$, are hydrogen or methoxy.

12. A process for converting a monophosphonate of formula Ia

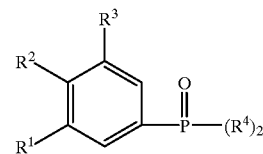

wherein
$R^1$ and $R^2$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; or
$R^1$ and $R^2$ together signify a fused benzene ring, a fused substituted benzene ring, a tetramethylene, trimethylene, methylenedioxo, ethylenedioxo group or a system of formula a

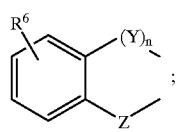

a

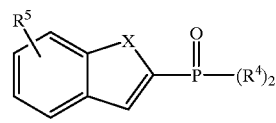

IIa $R^3$ and $R^6$ each independently signify hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino; and $R^4$ signifies phenyl, substituted phenyl, naphthyl, substituted naphthyl, heteroaryl, or substituted heteroaryl;

to a bisphosphonate of formula I

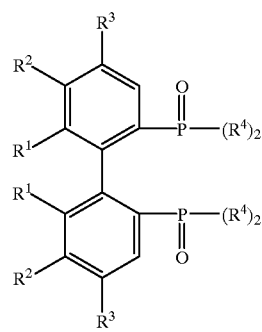

I wherein $R^1$, $R^2$, $R^3$ and $R^4$ are as above,

Y signifies $CR^7R^8$, O, S or N-$C_{1-8}$-alkyl;

Z signifies O, S, SO or $SO_2$;

n signifies 0 or 1;

$R^7$, $R^8$ each independently signify hydrogen or $C_{1-8}$-alkyl;

with the proviso that $R^4$ is not phenyl when $R^1$ and $R^2$ together signify methylenedioxy;

comprising treating said monophosphonate with a $C_1$–$C_8$ alkyllithium or aryllithium in an organic solvent to form a suspension, and thereafter oxidizing said treated monophosphonate in the resulting suspension with an oxidatively-acting metal salt to convert said treated monophosphonate to said bisphosphonate.

13. The process of claim 12 wherein the metal in the oxidatively acting metal salt is selected from the group consisting of vanadium, chromium, manganese, iron, cobalt, nickel, copper, silver, gold, ruthenium and molybdenum.

14. A process of claim 2 wherein the compound of formula 1a is reacted with tert-butyllithium or phenyllithium.

15. A process of claim 12 wherein the oxidatively acting metal salt is $FeCl_3$.

16. A process of claim 15 wherein the amount of $FeCl_3$ is 1.0 to 2.0 eq.

17. A process of claim 2 wherein R4 is phenyl or phenyl substituted with methoxy.

18. A process of claim 2 wherein R1, R2, and R3 are hydrogen or methoxy.

19. A process for converting a monophosphonate of formula Ia wherein

X signifies O or S;

$R^4$ signifies $C_{1-8}$-alkoxy, phenyloxy, or substituted phenyloxy, phenyl, substituted phenyl, naphthyl, substituted naphthyl, heteroaryl, or substituted heteroaryl; and $R^5$ signifies hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;

to a bisphosphonate of formula II

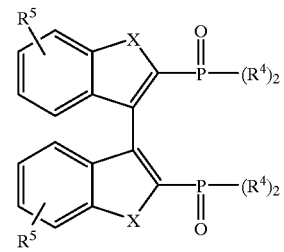

II wherein

X and $R^5$ are as above; and $R^4$ signifies $C_{1-8}$-alkoxy, phenyloxy, substituted phenyloxy, $C_{1-8}$-alkyl, or $C_{3-7}$-cycloalkyl, phenyl, substituted phenyl, naphthyl, substituted naphthyl, heteroaryl, or substituted heteroaryl;

comprising treating said monophosphonate with a compound of formula b1 or b2

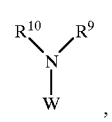

b1

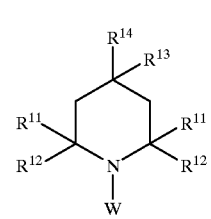

b2 wherein $R^9$ signifies $C_{1-8}$-alkyl, $C_{3-6}$-cycloalkyl or phenyl;

$R^{10}$ signifies $C_{1-8}$-alkyl or $C_{3-6}$-cycloalkyl;

$R^{11}$ and $R^{12}$ signify the same or different $C_{1-8}$-alkyl groups;

$R^{13}$ and $R^{14}$ each independently signify hydrogen or $C_{1-8}$-alkoxy; or $R^{13}$ signifies hydrogen or $C_{1-8}$-alkyl and $R^{14}$ signifies OW; or $R^{13}$ and $R^{14}$ together signify a ketal grouping selected from the group consisting of formulae c–e

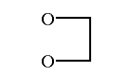

c

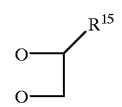

d

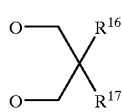

e $R^{15}$ signifies $C_{1-8}$-alkyl;

$R^{16}$ and $R^{17}$ signify hydrogen or the same or different $C_{1-8}$-alkyl groups; and W signifies lithium, magnesium chloride, bromide, or iodide, or magnesium amide;

in an organic solvent to form a suspension, and thereafter oxidizing said treated monophosphonate in the resulting suspension with an oxidatively-acting metal salt to convert said treated monophosphonate to said bisphosphonate.

20. The process of claim 19 wherein the metal in the oxidatively acting metal salt is selected from the group consisting of vanadium, chromium, manganese, iron, cobalt, nickel, copper, silver, gold, ruthenium and molybdenum.

21. A process of claim 19 wherein a catalytic amount of the compound formula b1 or b2 is used in the presence of $C_{1-8}$ alkyllithium or aryllithium.

22. A process of claim 19 wherein the oxidatively acting metal salt is $FeCl_3$.

23. A process of claim 22 wherein the amount of $FeCl_3$ is 1.0 to 2.0 eq.

24. A process of claim 19 wherein the compound of formula 1a is reacted with a compound of formula b1.

25. A process of claim 24 wherein $R^9$ and $R^{10}$ are isopropyl and W is lithium in the compound of formula b1.

26. A process of claim 19 wherein the compound of formula 1a is reacted with a compound of formula b2.

27. A process of claim 26 wherein $R^{11}$ and $R^{12}$ are methyl, $R^{13}$ and $R^{14}$ are hydrogen, and W is lithium in the compound of formula b2.

28. A process of claim 19 wherein $R^4$ is phenyl or phenyl substituted with methoxy.

29. A process of claim 19 wherein $R^5$ is hydrogen.

30. A process of claim 19 wherein X is sulfur.

31. A process for converting a monophosphonate of formula IIa

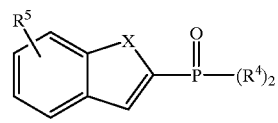

IIa wherein

X signifies O or S;

$R^4$ signifies $C_{1-8}$-alkoxy, phenyloxy, or substituted phenyloxy, phenyl, substituted phenyl, naphthyl, substituted naphthyl, heteroaryl, or substituted heteroaryl; and $R^5$ signifies hydrogen, $C_{1-8}$-alkyl, phenyl, substituted phenyl, $C_{1-8}$-alkoxy, phenyloxy, substituted phenyloxy, benzyloxy, substituted benzyloxy, halogen or di-$C_{1-8}$-alkylamino;

to a bisphosphonate of formula II

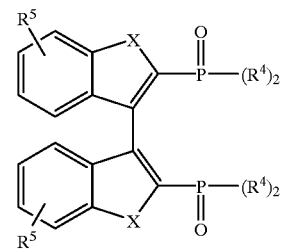

II wherein

X and $R^5$ are as above; and $R^4$ signifies $C_{1-8}$-alkoxy, phenyloxy, substituted phenyloxy, $C_{1-8}$-alkyl, or $C_{3-7}$-cycloalkyl, phenyl, substituted phenyl, naphthyl, substituted naphthyl, heteroaryl, or substituted heteroaryl;

comprising treating said monophosphonate with a $C_{1-8}$ alkyllithium or a aryllithium in an organic solvent to form a suspension, and thereafter oxidizing said treated monophosphonate in the resulting suspension with an oxidatively-acting metal salt to convert said treated monophosphonate to said bisphosphonate.

32. The process of claim 31 wherein the metal in the oxidatively acting metal salt is selected from the group consisting of vanadium, chromium, manganese, iron, cobalt, nickel, copper, silver, gold, ruthenium and molybdenum.

33. A process of claim 31 wherein the compound of formula 1a is reacted with tert-butyllithium or phenyllithium.

34. A process of claim 31 wherein the oxidatively acting metal salt is $FeCl_3$.

35. A process of claim 31 wherein $R^4$ is phenyl or phenyl substituted with methoxy.

36. A process of claim 31 wherein $R^5$ is hydrogen.

37. A process of claim 31 wherein X is sulfur.

* * * * *

UNITED STATES PATENT AND TRADEMARK OFFICE
CERTIFICATE OF CORRECTION

PATENT NO.   : 6,162,929
DATED        : December 19, 2000
INVENTOR(S)  : Joseph Foricher et al.

Page 1 of 1

It is certified that error appears in the above-identified patent and that said Letters Patent is hereby corrected as shown below:

Column 25, claim 14,
Line 54, replace "2" with -- 12 --.

Column 25, claim 17,
Line 62, replace "2" with -- 12 --.

Column 25, claim 18,
Line 63, replace "2" with -- 12 --.

Column 25, claim 19,
Line 67, replace "Ia" with -- IIa --.

Signed and Sealed this

First Day of January, 2002

Attest:

Attesting Officer

JAMES E. ROGAN
Director of the United States Patent and Trademark Office